United States Patent [19]
Errico et al.

[11] Patent Number: 5,876,402
[45] Date of Patent: Mar. 2, 1999

[54] ANTERIOR SPINAL POLYAXIAL LOCKING SCREW PLATE ASSEMBLY HAVING RECESSED RETAINING RINGS

[76] Inventors: Joseph P. Errico, 150 Douglas Rd., Far Hills, N.J. 07931; Thomas J. Errico, 5 Crest Acre Ct., Summit, N.J. 07901; James D. Ralph, 71 Manito Ave., Oakland, N.J. 07436

[21] Appl. No.: 624,110

[22] Filed: Mar. 29, 1996

Related U.S. Application Data

[63] Continuation-in-part of Ser. No. 421,087, Apr. 13, 1995, Pat. No. 5,520,690.

[51] Int. Cl.$^6$ ..................................................... A61B 17/70
[52] U.S. Cl. ................................. 606/61; 606/69; 606/70; 606/73
[58] Field of Search ................................. 606/69, 70, 71, 606/61, 60, 72, 73, 75, 76, 104; 623/16, 17

[56] References Cited

U.S. PATENT DOCUMENTS

5,057,111  10/1991  Park ........................................... 606/69
5,520,690  5/1996  Errico et al. ............................... 606/61

Primary Examiner—Guy V. Tucker

[57] ABSTRACT

The present invention is a polyaxial locking screw plate assembly for immobilization of vertebral bones, via fixation to surfaces thereof. The assembly includes a plate, having an upper portion and a lower portion, each of which has a pair of tapered holes, into which holes coupling elements and bone screws may be inserted. The upper part of the holes further includes an annularly recessed channel in which a snap-ring is disposed. The coupling elements each have an axial taper which matches the taper of the holes, and an interior semi-spherical concave surface in which the semi-spherical head of a bone screw may be polyaxially mounted. The bone screws are inserted through the holes until the coupling element engages and expands the snap-ring. Once the coupling element is fully seated in the hole, thereby locking the screw in place and the coupling element in the hole, the snap-ring contracts to its undeflected position and prevents the coupling element and screw from backing out of the hole in the event of loosening.

7 Claims, 6 Drawing Sheets

ANTERIOR SPINAL POLYAXIAL LOCKING SCREW PLATE ASSEMBLY HAVING RECESSED RETAINING RINGS

CROSS REFERENCE A TO RELATED APPLICATION

This application is a continuation-in-part of application U.S. Ser. No. 08/421,087, entitled "Anterior Spinal Polyaxial Locking Screw Plate Assembly", filed Apr. 13, 1995 now U.S. Pat. No. 5,520,690.

BACKGROUND OF THE INVENTION

1. Field of the Invention

This invention relates generally to a spinal implant assembly for holding adjacent vertebral bones fixed. More particularly, this invention relates to a novel assembly of bone screws and plates for use in surgical procedures for stabilizing the relative motion of, or permanently immobilizing, vertebral bodies, wherein the screws form a polyaxial coupling of the plate to the bone, and which maintains a flush exterior plate surface through a wide range of entrance angulation.

2. Description of the Prior Art

The bones and connective tissue of an adult human spinal column consists of more than 20 discrete bones coupled sequentially to one another by a tri-joint complex which consist of an anterior disc and the two posterior facet joints, the anterior discs of adjacent bones being cushioned by cartilage spacers referred to as intervertebral discs. These more than 20 bones are anatomically categorized as being members of one of four classifications: cervical, thoracic, lumbar, or sacral. The cervical portion of the spine, which comprises the top of the spine, up to the base of the skull, includes the first 7 vertebrae. The intermediate 12 bones are the thoracic vertebrae, and connect to the lower spine comprising the 5 lumbar vertebrae. The base of the spine is the sacral bones (including the coccyx). The component bones of the cervical spine are generally smaller than those of the thoracic spine, which are in turn smaller than those of the lumbar region. The sacral region connects laterally to the pelvis. While the sacral region is an integral part of the spine, for the purposes of fusion surgeries and for this disclosure, the word spine shall refer only to the cervical, thoracic, and lumbar regions.

Figure 1:
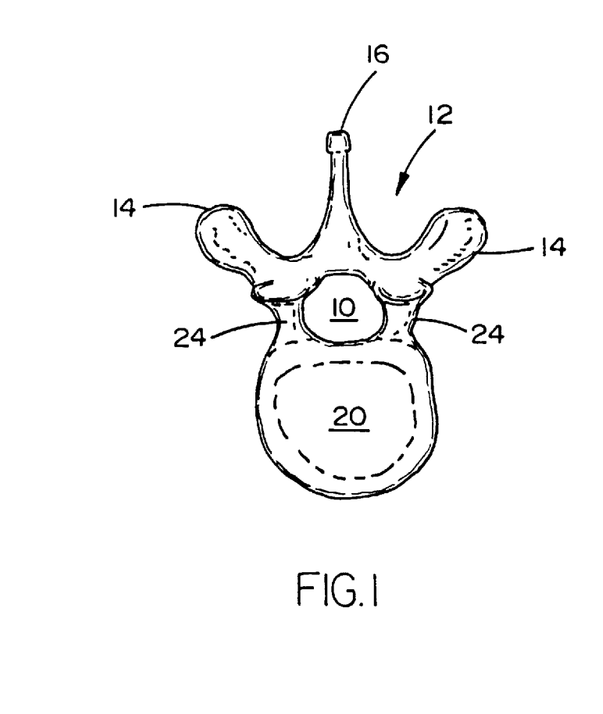
FIG. 1 is a top view of a vertebral bone, the stabilization of which the present invention is directed.
Figure 2:
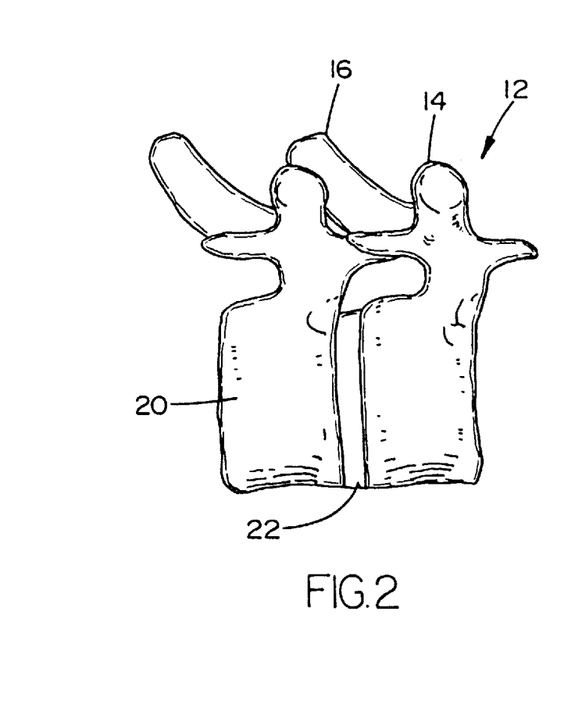
FIG. 2 is a side view of sequentially aligned vertebral bones.

Referring now to FIGS. 1 and 2, a typical vertebral body is shown in a top view and a side view. The spinal cord is housed in the central canal 10, protected from the posterior side by a shell of bone called the lamina 12. The lamina 12 has three large protrusions, two of these extend laterally from the shell and are referred to as the transverse process 14. The third extends back and down from the lamina and is called the spinous process 16. The anterior portion of the spine comprises a set of generally cylindrically shaped bones which are stacked one on top of the other. These portions of the vertebrae are referred to as the vertebral bodies 20, and are each separated from the other by the intervertebral discs 22. Pedicles 24 are bone bridges which couple the anterior vertebral body 20 to the corresponding lamina 12 and posterior elements 14,16.

The spinal column of bones is highly complex in that it includes over twenty bones coupled to one another, housing and protecting critical elements of the nervous system having innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and disease are a few of the causes which can result in spinal pathologies for which permanent immobilization of multiple vertebrae may be necessary. A variety of systems have been disclosed in the art which achieve this immobilization by implanting artificial assemblies in or on the spinal column. These assemblies may be classified as anterior, posterior, or lateral implants. As the classification suggests, posterior implants are attached to the back of the spinal column, generally hooking under the lamina and entering into the central canal, attaching to the transverse process, or coupling through the pedicle bone. Lateral and anterior assemblies are coupled to the vertebral bodies.

The region of the back which needs to be immobilized, as well as the individual variations in anatomy, determine the appropriate surgical protocol and implantation assembly. The use of screw plate assemblies for stabilization and immobilization via lateral or anterior entrance is, however, common.

Because the spine is routinely subject to high loads which cycle during movement, one of the primary concerns of physicians performing spinal implantation surgeries, as well as of the patients in whom the implants are placed, is the risk of screw pull-out. Screw pull-out occurs when the cylindrical portion of the bone which surrounds the inserted screw fails. A bone screw which is implanted perpendicular to the plate is particularly weak because the region of the bone which must fail for pull-out to occur is only as large as the outer diameter of the screw threads. It has been found that for pull-out to occur for a pair of screws which are angled inward, "toe nailed", or ones which diverge within the bone, the amount of bone which must fail increases substantially as compared to pairs of screws which are implanted in parallel along the axis that the loading force is applied. It has, therefore, been an object of those in the art to provide a screw plate assembly which permits the screws to be entered into the vertebral body at angles other than 90 degrees.

A great concern, however, with screws being implanted in the anterior portion spine, most particularly in the cervical spine, is that their are important internal tissue structures which, because of their proximity to the implant, may be damaged by a dislocated screw. In the cervical spine, the esophagus is located directly in front of the anterior surface of the vertebral body, and therefore, in potential contact with an implanted cervical plate. Breaches of the esophageal wall permit bacterial contamination of the surrounding tissues, including the critical nerves in and around the spinal cord. Such contamination can be fatal. Because screw pull-out represents one of the largest risks of esophageal perforation, it has been an object of those in the art to produce a cervical screw plate design having a locking means which couples, not only the plate to the bone, but locks the screw to the plate. In such a design, it is intended that, even if the bone holding the screw fails, the screw will not separate from the plate.

In addition to pull-out, however, it has been observed that if the screw plate design includes screw heads which protrude beyond the exterior surface of the plate, long term wearing of surrounding tissues may occur, leading to the development of abscesses and holes, which, once again, can have grave consequences. With respect to cervical plates, which are necessarily thin, on the order of a few millimeters, unless the system is designed to specifically accommodate non-perpendicular screw-in directions, the heads of the screws which are desirably toe-nailed in are a considerable risk.

Similar concerns exist in the thoracic and lumbar regions with respect to anterior and lateral fixation implants as their are proximally located organs as well as a plurality of major blood vessels which may be compromised by either catastrophic screw pull-out and/or long term wearing of non-flush surface protrusions.

One screw plate design which has been offered to provide physicians and patients with a reduced risk of pull-out or damage to proximal tissues is the Orion (Reg. Trademark) Anterior Cervical Plate System of Sofamor Danek USA, 1800 Pyramid Place, Memphis, Tenn. 38132. The Orion™ system teaches a plate having two pair of guide holes through which the screws are inserted to fix the plate to the vertebral body. The plate further includes external annular recessions about each of the guide holes which are radially non-symmetric in depth. More particularly, the annular recessions serve as specific angle guides for the screws so that they may be inserted non-perpendicularly with respect to the overall curvature of the plate. In addition, the Orion™ plate includes an additional threaded hole disposed between each of the pairs of guide holes so that a corresponding set screw may be inserted to lock the bone screws to the plate.

Although the Orion™ system achieved certain advantages over prior cervical screw plate assemblies, it is not without failures. Specifically, a given plate can accommodate only one screw-in angulation per hole, preferably in accordance with the angle of the annular recession. This is undesirable, in that physicians often must inspect the vertebral bodies during the implantation procedure before making the decision as to which screw-in angle is the ideal. By forcing the physician to chose from a limited set of angles, it is unavoidable that physicians will be forced to implant plates having screws which were positioned non-ideally. While providing a variety of plates having different angle guide holes and annular recession orientations is possible, the complexity and expense of providing a full spectrum of plates available in the operating room for the surgeon to choose from is undesirable. It is a failure of the system that one plate cannot accommodate a variety of different screw-in angles.

It is further a failure of the Orion™ system that an extra set screw is required to lock the screw to the plate. Plates for use in the cervical spine are very thin, and if the screw head already rests in an annular recess, and there is to be enough room for the head of the set screw to rest on top of the head of the bone screw, the thickness of the remaining plate must be reduced even further. The thinner the plate is at the load bearing points—the guide holes—the weaker the plate is overall.

While the preceding discussion has focused on a specific cervical screw plate system and its failures, the same failures apply to the art of vertebral immobilizing screw plate systems which are presently available as well. There are no presently available screw plate assemblies which present a flush surface and provide for means of preventing both screw pull-out from the bone and screw backout from the plate, while simultaneously providing for a wide range of angulation for the bone screws.

It is therefore, an object of the present invention to provide a new and novel cervical, thoracic, and/or lumbar screw plate design having a polyaxial coupling of the screw to the plate, whereby a single plate is compatible with a wide range of screw-in angles.

It is also an object of the present invention to provide an orthopedic screw plate assembly which has a simple and effective locking mechanism for locking the bone screw to the plate.

It is still further an object of the present invention to provide a screw plate assembly having a retaining means for preventing screw pull-out in the event of a failure of the locking mechanism.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a locking polyaxial screw plate assembly for use in stabilizing and immobilizing vertebral bodies. The assembly comprises: a plate having a plurality of tapered holes, each having recessed retaining snap-rings; bone screws having semi-spherical heads; and corresponding coupling elements.

The heads of the screws further comprise a recessed region such as a slot, phillips, star, or hexagonal recesses which are ideally suited for mating to an appropriate screw-driving tool. The recess, however, does not alter the exterior radially semi-spherical shape of the head.

The coupling elements have tapered external surfaces which match the taper of the corresponding through holes. Each coupling element further includes an interior volume which is semi-spherical to polyaxially retain the semi-spherical head of the corresponding screw. The coupling elements are axially slotted with one or more slots such that a radially applied force causes the interior volume to expand or contract according to the direction of the applied force. This expansion permits the head of the screw to be inserted into the interior volume; and the contraction provides for the crush locking of the interior surface of the coupling element to the head of the screw. Prior to use, each coupling element is joined with a corresponding screw. The coupling element must provide a recess or opening in the top thereof so that the screw and coupling element may be manipulated easily so that the recess in the head of the screw is accessible.

The retaining snap-rings are disposed in annular recessed channels in the upper portions of the tapered sidewall of the holes. The snap-ring, itself, is a flat, circumferentially discontinuous, circular element. The discontinuity in the element permits the ring to be radially compressed for insertion in the channel, and also to be expanded to permit the tapered coupling element to slide through it into the hole. After the coupling element passes through it, however, the ring snaps back into its undeflected shape which fits loosely in the recessed channel, and extends radially inward to block the element from backing out of the hole.

The first step in the process of implanting this invention is to position the plate against the vertebral bodies and to align the entry points for the screws. Next, pre-drilled holes are formed in the bones at the desired angle, into which the screws are to be inserted. With the plate in place, the screws are inserted through the holes and into the vertebral bodies. Once the screw has been inserted into the bone, at the desired angle, the coupling element, via its rotationally free mating of the socket to the inserted screw, is realigned so that it seats into the hole. Continued screwing down causes the bottom of the coupling element to advance into the hole, passing through the retaining ring. As the tapered surface of the coupling element advances, the retaining ring spreads apart, expanding into the annular recessed channel. Once the coupling element fully passes the retaining snap-ring, the ring elastically contracts back to its undeflected conformation (which is narrower than the diameter of the top of the coupling element), therein preventing the coupling element from backing out by interference.

The final seating of the coupling element in the depth of the tapered hole causes the element to contract slightly (as the axial slot or slots are narrowed). This contraction causes the interior volume to crush-lock to the semi-spherical head of the screw thereby locking it at the given angulation. Simultaneously, the coupling element is expansion locked to the inner surface of the hole by friction.

DETAILED DESCRIPTION OF THE PREFERRED EMBODIMENT

While the present invention will be described more fully hereinafter with reference to the accompanying drawings, in which particular embodiments and methods of fabrication are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope. Like numbers refer to similar features of like elements throughout.

Figure 3A:
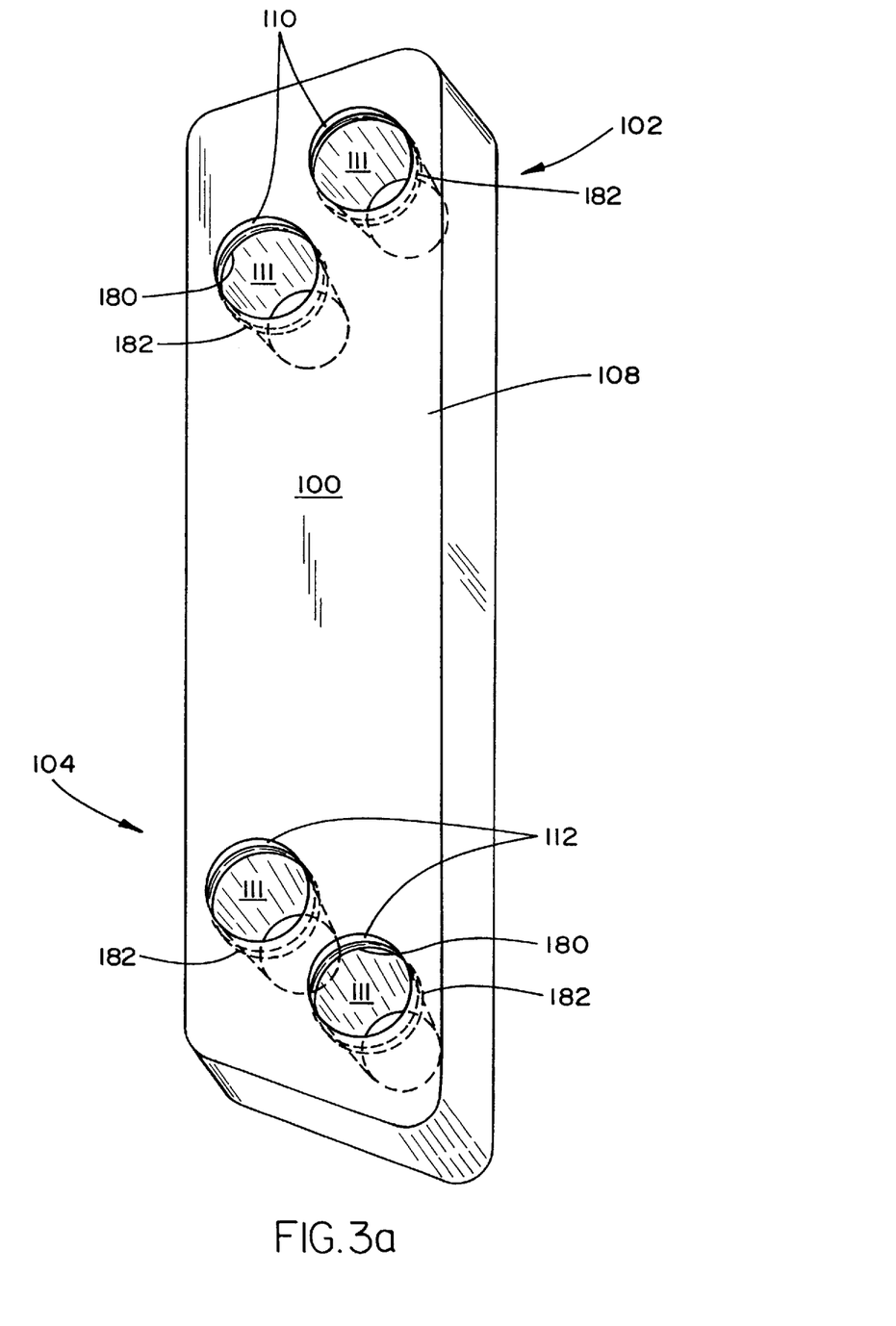
FIGS. 3a and 3b are perspective and top views, respectively, of a locking plate having retaining snap-rings which is an element of the present invention.
Figure 3B:
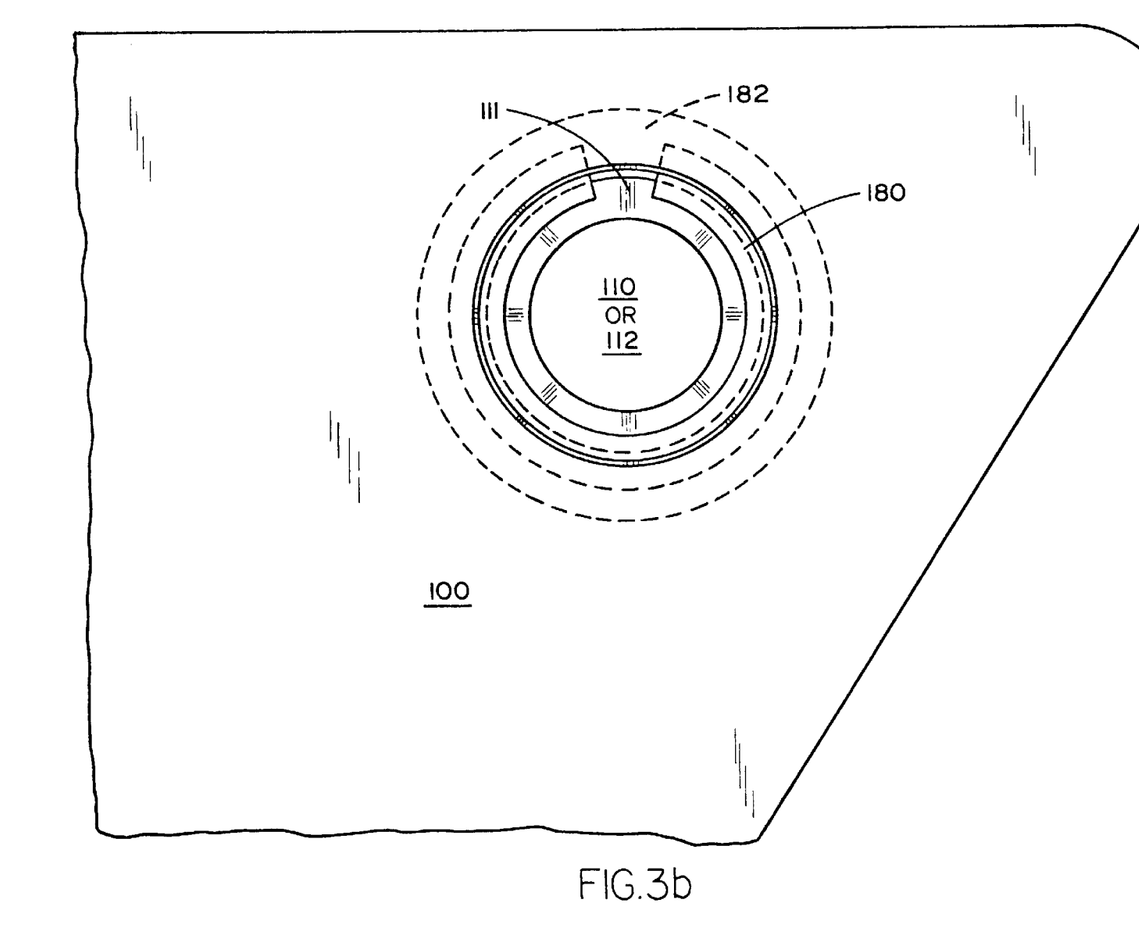

Referring now to FIGS. 3a and 3b, a plate which is an element of the present invention is shown in perspective and top views, respectively. The plate 100 may be constructed of any suitably biocompatible material which has the structural strength and durability to withstand the cyclical loading associated with long term fixation to the spine. Materials which would be suitable for such applications include titanium alloys and steels. A specific titanium material which has been utilized in implants of the prior art include ASTM F-136 titanium alloy (Ti 6AL-4V). This material has enhanced mechanical properties including fatigue endurance and tensile strength, as compared with pure titanium.

The plate 100 comprises upper and lower portions 102, 104 respectively, and a top surface 108 and a bottom surface (not shown). A slight curvature may be imparted to the plate 100 so that it may grossly conform to the cylindrical morphology of the bones (i.e., vertebral bodies) which it couples. The curvature would correspondingly be such that the top surface 108 would be convex surface, and the bottom surface would be concave.

A pair of holes 110, having a smooth tapered inner surface 111, extend fully through the upper portion 102 of the plate. A second pair of holes 112 having a tapered inner surface 111 as well, are disposed in the lower portion 104 of the plate 100. Each of the holes 110,112 is ideally suited for receiving therethrough a bone screw for affixing the plate to the vertebral bodies.

Referring also to FIG. 3b, each of the holes 110 or 112 includes an annular recessed channel 182. Within this annular recess 182 is provided a discontinuous "7/8ths" snap-ring 180. The undeflected outer diameter of the snap-ring is greater than the diameter of the hole 110 or 112 (so that it will remain in the recess), and the inner diameter of the undeflected snap-ring 180 is less than the diameter of the tapered hole. This permits the snap-ring 180 to protrude as an annular flange into the hole 110 or 112 in its undeflected state. The ring 180 can, however, be deflected inward or outward so as to entirely seat within the annular channel, or be removed entirely from the hole.

Figure 4:
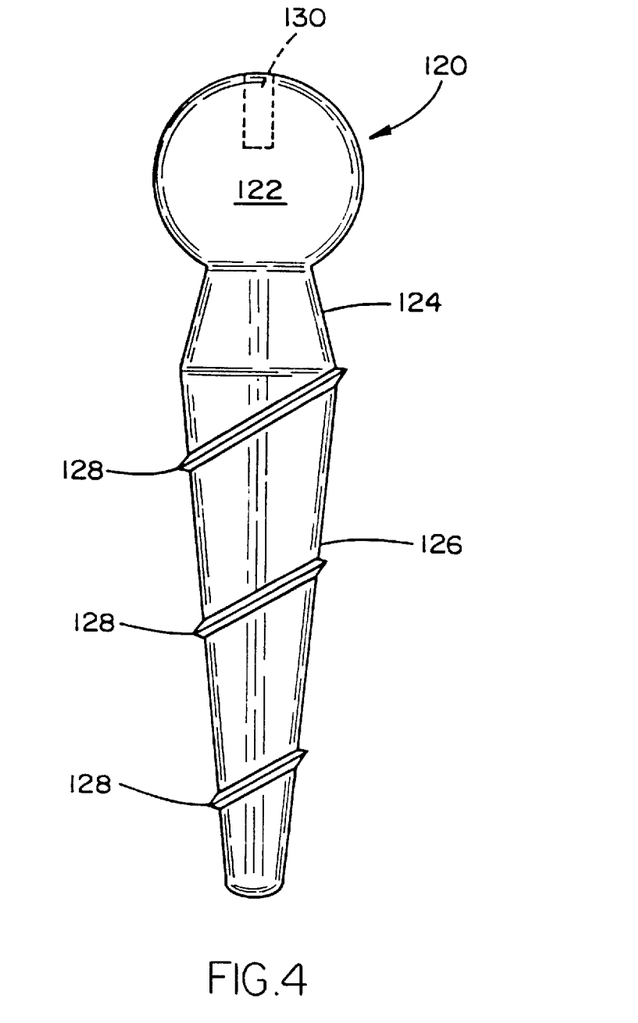
FIG. 4 is a perspective view of a bone screw of the present invention.

Referring now to FIG. 4, a screw of a type which is ideally suited for coupling the plates of this invention to vertebral bodies (or long bones in other embodiments) is shown in a side view. The screw 120 comprises a head portion 122, a neck 124, and a shaft 126. In FIG. 4, the shaft 126 is shown as having a tapered shape with a high pitch thread 128. It shall be understood that a variety of shaft designs are interchangeable with the present design. The specific choice of shaft features, such as thread pitch, or shaft diameter to thread diameter ratio, or overall shaft shape, etc. should be made be the physician with respect to the conditions of the patient's bone, however, this invention is compatible with a wide variety of shaft designs.

The head portion 122 of the screw 120 comprises a semi-spherical shape, which has a recess 130 in it. It is understood that the semi-spherical shape is necessarily is a section of a sphere, greater in extent than a hemisphere, and exhibits an external contour which is equidistant from a center point of the head. In a preferred embodiment, the major cross-section of the semi-spherical head 122 (as shown in the two dimensional illustration of FIG. 4) includes at least 270 degrees of a circle.

The recess 130 defines a receiving locus for the application of a torque for driving the screw 120 into the bone. The specific shape of the recess 122 may be chosen to cooperate with any suitable screwdriving tool. For example, the recess 130 may comprise a slot for a flat-headed screwdriver, a crossed recess for a phillips head screwdriver, a hexagonally shaped hole for receiving an alien wrench, or most preferably, a threading for receiving a correspondingly threaded post. It is further preferable that the recess 130 be co-axial with the general elongate axis of the screw 120, and most particularly with respect to the shaft 126. Having the axes of the recess 130 and the shaft 126 co-linear facilitates the step of inserting the screw 120 into the bone.

The semi-spherical head portion 122 is connected to the shaft 126 at a neck portion 124. While it is preferable that the diameter of the shaft 126 be less than the radius of the semi-spherical head 122, it is also preferable that the neck 124 of the screw 120 be narrower than the widest portion of the shaft 126. This preferable dimension permits the screw to be inserted at a variety of angles while still permitting the specific coupling element to be screwed into the appropriate hole 110 or 112 of the plate 100 and remain coupled to the head 122.

Figure 5:
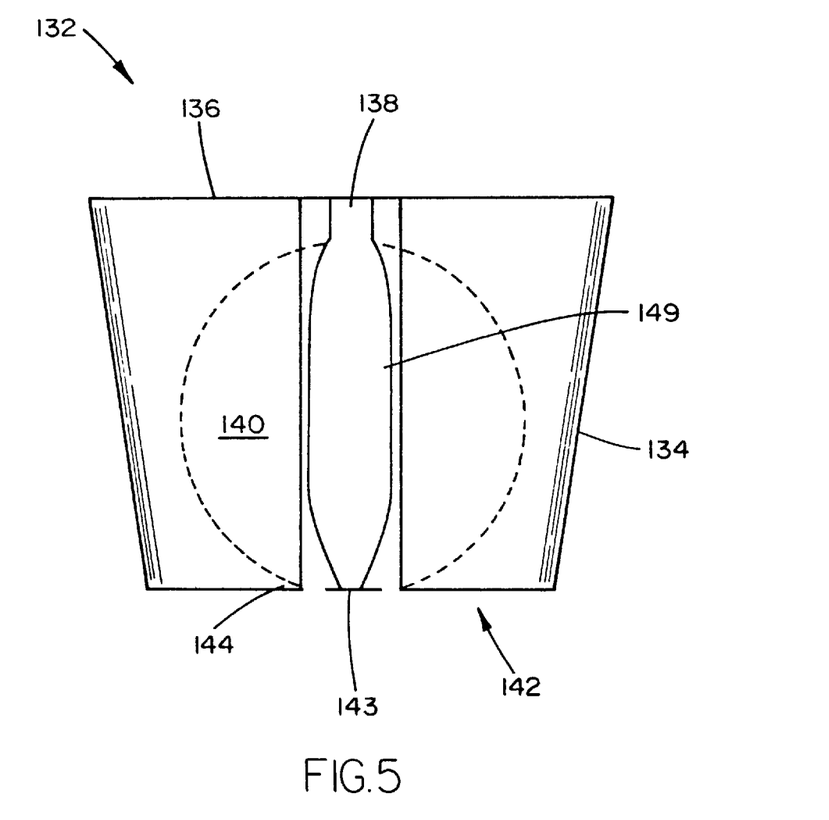
FIG. 5 is a side view of the coupling element receives the bone screw as shown in FIG. 4.

Referring now also to FIG. 5 the coupling element 132, which is utilized in conjunction with the plate 100 shown in FIG. 3, is shown in a side view, wherein phantom lines show the interior structure of the element along a diametrical cross section. The coupling element 132 comprises a tapered cylindrical socket having a smooth external surface 134. The taper of the surface 134 is designed to mate with the interior tapered surface 111 of the holes 110 or 112 of the plate 100, so that the coupling element 132 may be seated into the plate 100.

The top surface 136 of the coupling element 132 further comprises a through hole 138, which extends from the top surface 136 to an interior semi-spherical volume 140. This through hole 138 is designed such that the screwdriving tool which is used to insert the screw 120 into the bone may access and rotate the screw 120 through the coupling element.

The coupling element 132 further includes an interior semi-spherical volume 140 which is ideally suited for holding the head portion 122 of the screw 120, and permitting the screw to rotate through a range of angles. The bottom 142 of the coupling element 132 has a circular hole (enumerated as 143 on the bottom surface of the side view of the coupling element) which forms the bottom entrance into the interior semi-spherical volume 140. It is understood that the head 122 of the screw 120 is held within the interior semi-spherical volume 140 by the annular rim, or support lip, 144 of the bottom 142 of the coupling element. This annular support lip 144 defines the circular opening 143 which has a diameter less than the diameter of the semi-spherical head 122 of the screw 120, but larger than the neck 124 of the screw 120 (so that the screw 120 may polyaxially rotate relative to the coupling element 132 once the head 122 has been inserted into the interior volume 140.

The coupling element 132 may comprise a plurality of axial slots which extend axially upward part of the way from the bottom of the element to the top, however, in a preferred embodiment, the element 132 comprises a single axial slot 149 which extends fully up the element 132 so that it has a circumferentially discontinuous conformation. This renders the coupling element 132 a 7/8ths collar, and permits the element 132 to expand to accept the inserted head portion 122, and also to crush against the head 122 upon the application of an inwardly directed radial force. Insertion of the coupling elements into the through holes prevents the coupling elements from releasing the head 122 by preventing the circular opening 143 from expanding.

Figure 6:
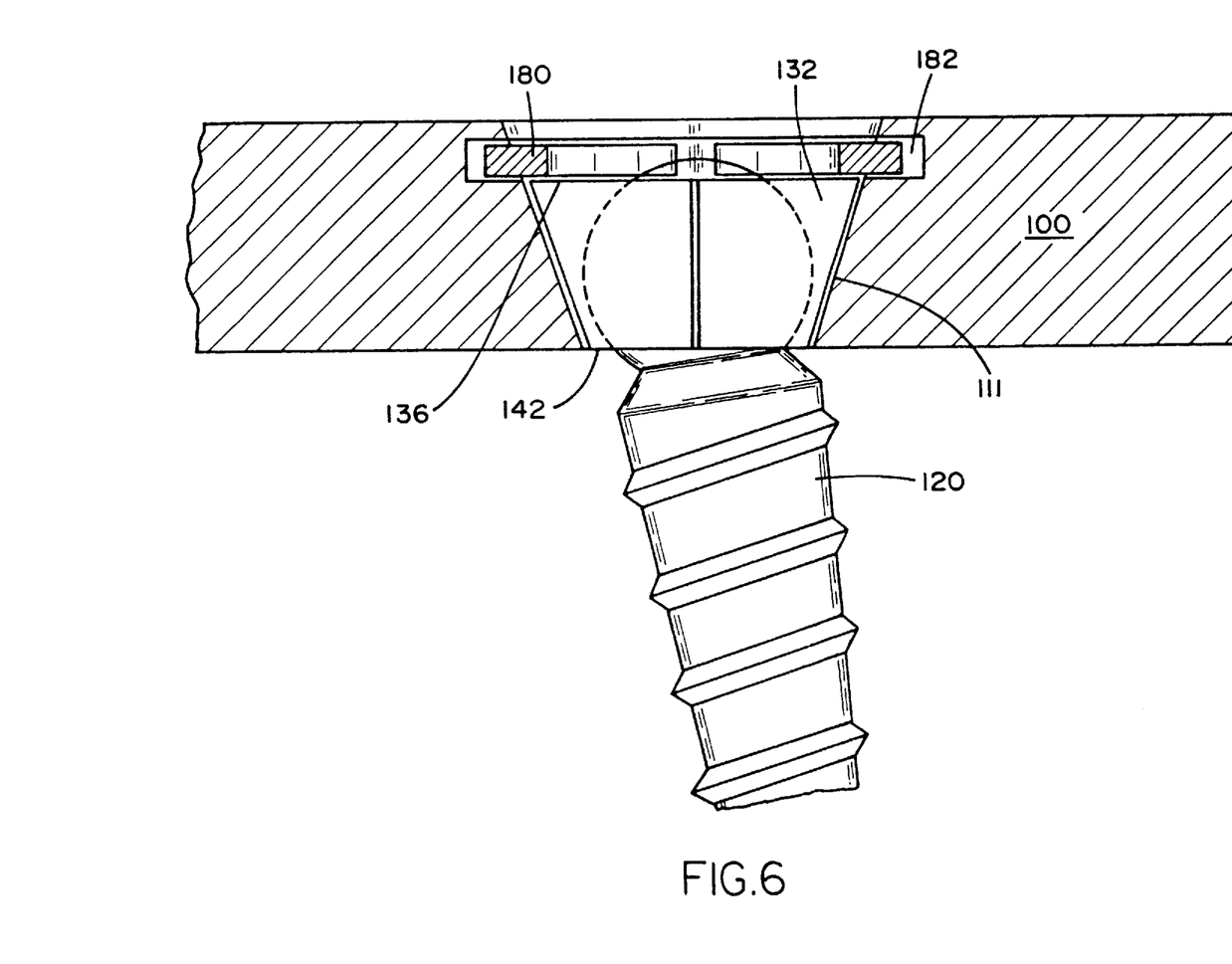
FIG. 6 is a side cross-section view of a fully assembled embodiment of the present invention.

Referring now to FIG. 6, the assembled screw 120, coupling element 132, snap-ring 180 and plate 100 are shown in a cross-section view. The snap-ring 180 is deflected inward for positioning in the recess 182. During the implantation procedure, the screw 120 and the coupling element 132 are inserted through the hole. Once the bottom 142 of the coupling element 132, respectively, seats in the top of the hole 110 or 112, and begins to travel into it, the tapered exterior surface of the coupling element 132 causes the snap-ring 180 to expand into the recess 182. Once the coupling element 132 is fully seated in the hole 110, the snap-ring 180 is freed from the outward radial pressure of the coupling element 132 and snaps back to its undeflected state. In its undeflected state it prevents the coupling element 132 from backing out of the plate 100 inasmuch as the flat upper surface 136 of the coupling element is incapable of deflecting the ring outward (it has no taper to push the snap-ring open).

While there has been described and illustrated implantation devices for stabilizing and immobilizing regions of the spine by affixing a polyaxial locking screw plate to the anterior portion of the vertebral bones, it will be apparent to those skilled in the art that variations and modifications are possible without deviating from the broad spirit and principle of the present invention which shall be limited solely by the scope of the claims appended hereto.

We claim:

1. A polyaxial locking screw plate assembly the for immobilization of vertebral bones, via fixation to surfaces thereof, comprising:

a plate having a plurality of through holes; wherein at least one of said plurality of through holes includes an annular recess formed in an upper sidewall portion of said hole;

a snap-ring being disposed in said annular recess;

a corresponding plurality of coupling elements, each of said coupling elements being insertable into a corresponding one of said through holes; and a plurality of bone screws, each of said bone screws having a semi-spherical head portion and a shaft, said shaft portion being insertable through the corresponding through hole and into the bone, and said semi-spherical head portion being rotationally freely mounted in the coupling element prior to insertion and such that the shaft of the bone screw and the coupling element may be inserted into a corresponding through hole, said snap ring deflecting outward during the insertion of the coupling element to permit the coupling element into the through hole, and said snap ring snapping back to an undeflected condition once the coupling element has fully seated in the through hole, thereby preventing the coupling element from backing out of the through hole, and said shaft of the bone screw may be inserted into the bone at a selected angle within a predetermined range of angles including non-perpendicular angles relative to the plate and thereby locking said coupling element and said semi-spherical head to said plate at said selected angle.

2. The polyaxial locking screw plate assembly as set forth in claim 1, wherein said plate includes a first end and a second end, a first group of said through holes being disposed at said first end, and a second group of said through holes being disposed in said second end.

3. The polyaxial locking screw plate assembly as set forth in claim 1, wherein said coupling elements each comprise an interior semi-spherical volume, defined by a curved interior surface, which forms a receiving socket into which the semi-spherical head portion is inserted whereby the head portion of said screw is rotationally freely mounted in said coupling element.

4. The polyaxial locking screw plate assembly as set forth in claim 3, wherein said coupling element further comprises at least one slot which permits the interior semi-spherical volume to expand thereby facilitating the insertion of said semi-spherical head portion of said screw therein.

5. The polyaxial locking screw plate assembly as set forth in claim 4, wherein the corresponding through hole into which the coupling element is inserted is tapered inwardly, thereby causing, upon insertion of said coupling element into said corresponding through hole, the at least one slot to be narrow, causing the curved interior surface of the coupling element to lock the semi-spherical head portion of the screw at a definite insertion angle.

6. The polyaxial locking screw plate assembly as set forth in claim 1, wherein the head portion of each of said screws comprises a recess to which a screwdriving tool is mateable for inserting said screw through the corresponding hole and into the bone.

7. The polyaxial locking screw plate assembly as set forth in claim 6, wherein each of said coupling elements comprises a top surface recess, through which said screwdriving tool may be inserted, and which top surface recess may be aligned with the recess in the head of the screw, by which screwdriver the screw may be inserted into the bone.

* * * * *